United States Patent [19]

Brown et al.

[11] Patent Number: 5,705,691
[45] Date of Patent: Jan. 6, 1998

[54] CHEMICAL PROCESS

[75] Inventors: Stephen M. Brown; James P. Muxworthy, both of Huddersfield; Gareth DeBoos, Ramsbottom, all of United Kingdom

[73] Assignee: Zeneca Limited, London, United Kingdom

[21] Appl. No.: 676,788

[22] Filed: Jul. 8, 1996

[30] Foreign Application Priority Data

Jul. 10, 1995 [GB] United Kingdom .................... 9514031

[51] Int. Cl.⁶ .................................................. L07C 303/38
[52] U.S. Cl. ........................... 564/99; 564/84; 564/91; 564/98
[58] Field of Search ........................... 564/99, 94, 91, 564/98

[56] References Cited

U.S. PATENT DOCUMENTS

| 3,622,626 | 11/1971 | Moore ........................ 260/556 |
| 4,835,312 | 5/1989 | Itoh et al. .................... 564/205 |
| 5,205,853 | 4/1993 | Wolf et al. .................... 504/247 |
| 5,256,632 | 10/1993 | Wolf et al. .................... 504/252 |

FOREIGN PATENT DOCUMENTS

| 0 027 837 | 5/1981 | European Pat. Off. . |
| 0 459 244 | 12/1991 | European Pat. Off. . |
| 0 508 796 | 10/1992 | European Pat. Off. . |
| 2 014 565 | 8/1979 | United Kingdom . |

OTHER PUBLICATIONS

Cossu, S., et al., "Unusual Reactivity of 4-Carboxyamido-2-oxazoline Systems: New Synthesis of Optically Active N-Sulphonyl Derivatives", Tetrahedron, vol. 50, No. 17, 1994, pp. 5083-5090.

Soloducho, J., "Synthesis of Some Pyrido[3,2-g][1,2,5] Triazocine Derivatives", Pol. J. Chem., vol. 59, 1985, pp.1115-1120.

Illi, V.O., "Phasentransfer-katalysierte N-Sulfonierung von Indol", Synthesis, No. 2, 1979, p. 136.

Primary Examiner—Peter O'Sullivan
Attorney, Agent, or Firm—Joseph R. Snyder

[57] ABSTRACT

A process for the preparation of an N-(alkylsulphonyl) amide, the process comprising reacting a primary amide with a sulphonyl halide in the presence of a base which is sufficiently strong to cause at least partial deprotonation of the amide.

9 Claims, No Drawings

CHEMICAL PROCESS

The present invention relates to a process for the preparation of N-(alksulphonyl)amides and N-(arylsulphonyl)amides, in particular those derived from, primary or aryl amides.

Sulphonamide substituted compounds are useful in many areas of chemistry, for example, agrochemicals, pharmaceuticals, polymers etc. However, although useful, N-(alkylsulphonyl)amides are not, in general, easy to synthesise, particularly those which are derived from primary amides. It is for that secondary amides and imides are capable of reacting with sulphonyl halides such as methane suphonyl chloride, to give secondary N-(alkylsulphonyl) amides or N-(alkylsulphonyl)imides and such reactions are well described in the literature, for example by Dorn et al (*Justus Liebigs Ann. Chem.*, (1967) 707, 100), Nagata et al (*Justus Liebigs Ann. Chem.*, (1961), 641, 184), Yoshioka et al (*J. Am. Chem. Soc.* (1984) 106, 1133) and Heller (*J. Chem. Eng. Data*, (1970) 15, 351)

However, this reaction has not been successfully applied to primary amides. Because of the extra hydrogen atom present in the system, these compounds tend to be dehydrated to give nitriles instead of reacting with the sulphonyl halide. Again, such reactions are described in the literature by for example, Dunn (*Org. Prep. Proced. Int.*, (1982), 14, 396) who describes the reaction of a primary amide with methane sulphonyl chloride in pyridine. The reaction proceeds via a dehydration route and the product is a nitrile. Brewster et al (*J. Am. Chem. Soc.* (1955) 77, 4564) also describe the reaction of a primary amide, 3-(2-hydroxycycloheyxl)propanamide, with toluene sulphonyl chloride, again in pryidine. This reaction also proceeds via a dehydration mechanism to give a nitrile which rearranges to a cyclic sulphonimide.

Such dehydration is, of course, impossible when secondary amides or imides are used but it has always presented a barrier to the synthesis of sulphonamides from primary amides.

Therefore, in the past, it has been necessary to prepare primary N-(alkylsulphonyl)amides by reaction of the corresponding acyl or aroyl halide with an alkane sulphonamide. For example, an acyl chloride may be reacted with methane sulphonamide in the presence of a base to yield the required product. This route, however, has the disadvantage that alkane sulphonamides such as methane sulphonamide are both expensive and difficult to produce and so, clearly, commercial advantage would be gained if cheaper reagents such as methane sulphonyl chloride could be used.

The present inventors have, for the first time, developed a process which makes possible the preparation of N-(alkylsulphonyl) primary amides.

Therefore, in a first aspect of the present invention, there is provided a process for the preparation of an N-(alkylsulphonyl)amide, the process comprising reacting a primary amide with a sulphonyl halide in the presence of a base which is sufficiently strong to cause at least partial deprotonation of the amide.

This method provides a simple and cost effective route for the conversion of primary amides to N-(alkylsulphonyl) amides. GB-A-2014565 describes an N-(alkylsulphonyl) amide-substituted diphenylether herbicide. One of the processes for preparing this herbicide is shown in Scheme B of the document and includes a step in which a primary amide is convened to an N-(alkylsulphonyl)amide by treatment with an alkane sulphonyl chloride in the presence of pyridine. At the time, it was assumed that this process would be successful because it is an extrapolation of successful methods for preparing secondary and tertiary N-(alkylsulphonyl) amides but it does not appear to be a method which was actually used. There are no specific examples in the document of the synthesis of primary N-(alkylsulphonyl)amides and, in practice, it proved impossible to repeat the suggested process using the conditions described since dehydration occurred and the product obtained was a nitrile. In view of this, it was particularly surprising that it has proved possible to effect this conversion using the reaction conditions of the present invention.

In the context of the present invention the term "sulphonyl halides" refers to sulphonyl halides substituted with an alkyl or aryl group. The alkyl group will in general, be a straight or branched alkane group having from 1 to 12 carbon atoms. Examples of such groups include methyl, ethyl, t-butyl, hexyl and dodecyl. For the most part, shorter chain alkyl having up to 4 carbon atoms, and in particular methane and ethane, sulphonyl halides are preferred. The aryl group will often be phenyl, benzyl or one of their derivatives. The benzene ring may be substituted with a substituent such as $C_1$-$C_4$ alkyl, chloro, fluoro, bromo, iodo, hydroxy or CN. Toluene sulphonyl halides are particularly preferred.

Any sulphonyl halide may be used, but, for reasons of economy, sulphonyl chlorides are especially preferred. Particularly suitable sulphonyl halides for use in the process of the present invention include methane, ethane and toluene sulphonyl chlorides. In the context of the present specification, the term "N-(alkylsulphonyl)amides" is also intended to encompass N-(arylsulphonyl)amides. Thus the products of the process of the present invention may have either an alkyl or an aryl group attached to the sulphonyl entity. The preferred aryl and alkyl groups are as specified above for sulphonyl halides. Although the process of the present invention can be used for the conversion of any primary amide to the N-(alkylsulphonylated) derivative, it is particularly successful when the starting material is a primary amide of an aromatic acid. The choice of base will, of course, depend on the starting material which is employed in the reaction and, in particular, on the acidity of the amide hydrogen. In most cases, however, the reaction proceeds successfully using a strong base such as an alkali metal, ammonium or quaternary ammonium hydroxide or an alkali metal hydride, for example sodium hydride.

Bases such as sodium amide, potassium bis-trimethylsilylamide and reducing metals such as sodium may also be successfully employed. For some starting materials it may not be necessary to use a base of this strength. As those skilled in the art will be aware, in the case of aromatic amides such as benzamide, the presence of electron withdrawing substituents in the aromatic ring system tends to make the amide hydrogen more acidic and so, for sulphonation of such aromatic amides, a weaker base such as an alkali metal carbonate or an alkaline earth metal hydroxide may sometimes be suitable. Thus, the necessary base strength will vary with the starting material and those skilled in the art will be able to select suitable bases for the reaction depending on the acidity of the amide group in the starting material.

The use of these bases, particularly strong bases such as sodium hydroxide, potassium hydroxide and sodium hydride, represents a significant departure from prior art processes for the conversion of secondary amides and imides to their N-(alkylsulphonylated) derivatives. For the most part such reactions have been conducted using bases such as pyridine which, when used to treat primary amides, convert them to nitriles via a dehydration mechanism.

The sulphonation reaction is greatly affected by the choice of solvent and among the most suitable solvents are co-ordinating solvents such as ethers, ketones, nitriles and dialkylamides. Tetrahydrofuran is a widely available and relatively low cost solvent which is particularly suitable for use in the process of the present invention but any of the other cyclic ether solvents, for example tetrahydropyran, could also be used. Co-ordinating solvents are useful when the base of choice has an alkali or alkaline earth metal cation because they are capable of co-ordinating to these cations and thus they can assist dissociation of the base even in a substantially non-aqueous system. Other solvent systems may also be used, for example a two phase system in which one phase may be aqueous and the other composed of an organic solvent such as toluene. The solvents which have been used in prior art reactions between amides and sulphonyl halides were generally non-polar solvents rather than co-ordinating solvents or two phase systems and this could account, at least in part, for the lack of success of previous attempts to sulphonylate primary amides.

In addition to the co-ordinating solvent, the reaction is also assisted by the presence of an agent that will react with the base to give an entity with a counter ion, typically an organic cation, which is soluble in the reaction solvent. An example of such an agent is tetrabutylammonium hydrogen sulphate which will react with a base such as sodium or potassium hydroxide to give tetrabutylammonium hydroxide. This compound is much more soluble in tetrahydrofuran than either sodium or potassium hydroxide and so the base is more accessible to the amide and the reaction proceeds faster with less chance of a dehydration side reaction. Other quaternary ammonium salts or organic cations can also be used for this purpose or, alternatively, a crown ether can be used to achieve the same objective.

The reaction may be carried out over a wide range of temperatures and can be conducted at any temperature from 0° to 100° C. although the reaction temperature will, of course be limited by the choice of solvent. When tetrahydrofuran is the chosen solvent, a suitable temperature range is from 10° to 70° C., preferably from about 45° to 60° C. As already briefly mentioned, the process of the invention is particularly suitable for the sulphonylation of aromatic primary amides, in particular benzamides. Since the acidity of the amide hydrogen is a key factor in the success of the process, any substituent which increases the acidity of the amide hydrogen will reduce the likelihood of a dehydration side-reaction. Thus, benzamides with electron withdrawing substituents in the aromatic ring can be converted to N-(alkylsulphonyl)benzamides by the process of the present invention more easily than can benzamides with electron releasing ring substituents. Therefore, aromatic primary amides with ring substituents such as nitro, cyano, halogen and other aromatic groups are particularly well suited to sulphonylation by the process of the invention. Examples of amides which can be sulphonylated by the process of the present invention are benzamide, mono-, di- and trinitrobenzamides, and compounds such as 3-(2-chloro-α, α, α-trifluoro-4-tolyloxy) benzamide and 5-(2-chloro-α, α, α-trifluoro-4-tolyloxy)-2-nitrobenzamide. These two latter compounds are both intermediates in the synthesis of 5-(2-chloro-α,α,α- trifluoro-4-tolyloxy)-N-methanesulphonyl-2-nitrobenzamide (also known as fomesafen) which is a well known herbicide.

The amide starting material will often be a compound which is readily available but, if not, it may be prepared in a variety of ways. Many methods for the preparation of amides are reported in literature and these include the reaction of a corresponding acyl halide, particularly the acid chloride, with ammonia. Thus, the present invention also provides an economical route for the conversion of acyl halides to N-(alkylsulphonyl)amides.

The reaction of the acyl halide with ammonia may be carried out in an organic solvent such as toluene or dichloromethane and the ammonia will preferably be added as an aqueous solution. The reaction should preferably be conducted at low temperature to avoid evaporation of the ammonia and a suitable reaction temperature is 0° to 10° C., preferably about 5° C. The resultant amide may then be convened to an N-(alkylsulphonyl)amide using the process described above.

After conversion of the acid chloride to the amide, the amide can either be converted to an N-(alkylsulphonyl) amide or there may be intervening steps, for example to introduce additional substituents into the aromatic ring of an aryl amide. If the final product of the reaction has ring substituents which are electronegative, it may be an advantage to introduce them before the conversion of the amide to the N-(alkylsulphonyl)amide since, as already discussed above, they will increase the acidity of the amide hydrogen and so assist the reaction. However, if the target molecule is an aryl N-(alkylsulphonyl)amide with electropositive ring substituents then it may be preferable to introduce them into the ring after the conversion of the amide to an N-(alkylsulphonyl)amide. It has been possible to convert acid chlorides to N-(alkylsulphonyl)amides using prior art methods but, as discussed above, the conversion was generally achieved by reaction of an acid chloride with a sulphonamide. Although the novel process of this invention involves two step reaction in which the acid chloride is first converted to an amide and then to an N-(alkylsulphonyl) amide, ammonia and sulphonyl halides are significantly less expensive reagents than, for example, methane sulphonamide and so the two step reaction can be still carried out more economically than prior art methods. A further factor which is worth noting is that both the reaction of the acyl halide and the reaction of the amide with the sulphonyl halide are, in general, high yielding and this further increases the economic viability of the invention.

An example of one use of the process of the present invention is in the synthesis of the herbicide 5-(2-α, α, α-trifluoro-4-tolyloxy)-N- methane-sulphonyl-2-nitrobenzamide (fomesafen) which may be prepared in two steps from 3-(2-chloro-α,α,α-trifluoro-4-tolyloxy.) benzamide.

Therefore, in a second aspect of the invention, there is provided a process for the synthesis of fomesafen from 3-(2-chloro-α,α,α-trifluoro-4-tolyloxy) benzamide, the process comprising, in any order, the steps of nitration and sulphonylation by a process according to the first aspect of the invention.

The nitration step may be carried out using any suitable method, for example by reaction with a nitrating agent such as nitric acid, optionally in the presence of sulphuric acid. Nitration methods are well known in the art.

Scheme I illustrates routes for the synthesis of fomesafen (V) from 3-(2-chloro-α,α,α-trifluoro-4-tolyloxy) benzoyl chloride (I). The first step is conversion to 3-(2-chloro-α, α, α-trifluoro-4-tolyloxy)benzamide (II) by any suitable method, for example by reaction with ammonia. This is followed by sulphonylation and nitration which may be carried out in either order.

Thus, when the sulphonylation step is carried out first, the process for the preparation of fomesafen comprises reacting 3-(2-chloro-α,α,α- trifluoro-4-tolyloxy) benzamide (III) with methane sulphonyl chloride in the presence of a base which is sufficiently strong to be capable of at least partially deprotonating the amide, and nitrating the product.

Alternatively, when nitration is the initial step, the process for the preparation of fomesafen comprises reacting 5-(2-chloro-α,α,α-trifluoro-4-tolyloxy)-2-nitrobenzamide (IV) with methane sulphonyl chloride in the presence of a base which is sufficiently strong to be capable of at least partially deprotonating the amide.

In either case, strong bases such as sodium or potassium hydroxide or sodium hydride may be used. However, since the amide hydrogen is relatively acidic, particularly in the case of the nitrated compound, it is also possible to use weaker bases such as potassium carbonate.

3-(2-Chloro-α,α,α-trifluoro-4-tolyloxy) benzamide (II) is a new compound which itself forms a further aspect of the invention and which may be prepared from 3-(2-chloro-α, α,α-trifluoro-4-tolyloxy) benzoyl chloride (I) by reaction with ammonia.

3-(2-Chloro-α,α,α-trifluoro-4-tolyloxy) benzoyl chloride (I) is a compound which is well known in the art and may be prepared by known methods.

The invention will now be described in greater detail with reference to the following examples.

EXAMPLE 1 a) Preparation of 3-(2-chloro-α,α,α-trifluoro-4-tolyloxy) benzamide

Into a 3 neck round bottom flask fitted with condenser and dropping funnel was added 3-(2-chloro-α,α,α-trifluoro-4-tolyloxy) benzoyl chloride (19.8 g 0.059 mol) and toluene (80 ml). The mixture was cooled in an ice bath to about 5° C. then ammonia solution 32% (15.6 g, 0.29 mol) was added dropwise. A yellow/orange precipitate formed and the mixture was stirred vigorously for 3 hours. The mixture was then extracted with toluene (200 ml) and washed with water (80 ml). The organic layer was separated, dried (MgSO$_4$), filtered and the solvent removed in vacuo. The resulting solid was then triturated with hexane to afford the product as a white solid (16.5 g, 91%). IR 1652 cm$^{-1}$ (amide C=O), 3376 and 3191 cm$^{-1}$ (N—H str);

MS E.I. m$^+$ (100%) 299 (m-NH$_2$), 236 (m-CF$_3$).

b) Reaction of 3-(2-chloro-α,α,α-trifluoro-4-tolyloxy) benzamide with methanesulphonyl chloride To the product of step (a) (5.0 g, 15.9 mmol) in THF (40 ml) was added potassium carbonate (3.7 g, 27.0 mmol), pulverised sodium hydroxide (3.36 g, 84.1 mol) and tetrabutylammonium hydrogen sulphate (0.27 g, 0.8 mmol). The mixture was stirred vigorously and heated to 50° C. A solution of methanesulphonyl chloride (2.36 g, 20.6 mmol) in THF (10 ml) was added dropwise over 20 minutes. The mixture was left stirring at 50° C. for a further 21 hours. The mixture was then allowed to cool to room temperature and extracted with ethyl acetate and washed with water. The ethyl acetate layer was separated and dried (MgSO$_4$), filtered and evaporated in vacuo to afford the crude product as an off white solid (6.2 g). Quantitative HPLC analysis showed the presence of the required sulphonamide (3.87 g, 62%). IR 1674 cm "(C=O)".

EXAMPLE 2 a) Nitration of 3-(2-chloro-α,α,α-trifluoro-4-tolyloxy) benzamide

Into a 2 neck 1 liter round bottom flask was added 98% sulphuric acid (538 g, 5.4 mol), this was then cooled to below 10° C. and water (28 g, 1.6 mol) added slowly. The mixture was then cooled below −10° C. (ice/sodium chloride bath). 3-(2-Chloro-α,α,α-trifluoro-4-tolyloxy) benzamide (13.0 g) and mixed sulphuric/nitric acid (32% nitrate acid) (8.4 g) followed by a further amount of 3-(2-chloro-α,α,α-trifluoro-4-tolyloxy) benzamide (13.0 g) were added. The mixture was stirred for 5 minutes then further portions of amide and mixed acid were added. This process was repeated until all the amide and nitric acid had been added allowing 5 minutes between each set of additions. The mixture was stirred for a further 2 hours then poured slowly onto crushed ice with good stirring. The resulting solid was then filtered off and dried under suction. The crude product was then recrystallised from ethyl acetate/hexane. 71.3 g, 84% product was obtained as a pale orange solid. IR 1668 cm$^{-1}$ (C=O) GC/MS m$^+$360.

b) Reaction of 5-(2-chloro-α,α,α-trifluoro-4-tolyloxy)-2-nitrobenzamide with methanesulphonyl chloride To the product of step (a) (1.99 g, 5.52 mmol) in THF (25 ml) was added potassium carbonate (1.29 g, 9.38 mmol), pulverised sodium hydroxide (1.16 g, 29.0 mmol) and tetrabutylammonium hydrogen sulphate (0.09 g, 0.28 mmol). The mixture was stirred vigorously and heated to 55° C. for 20 minutes then a solution of methanesulphonyl chloride (0.82 g, 7.2 mmol) in THF (5ml) was added dropwise over 10 minutes. The mixture was held at 50° C. for a further 4½ hours then allowed to cool to room temperature. The mixture was then adjusted to pH 4.0 using 1M hydrochloric acid and extracted with ethyl acetate. The ethyl acetate layer was washed with water then the organic layer was separated, dried (MgSO$_4$), filtered and evaporated in vacuo to afford the crude product as a brown solid (2.0 g).

Quantitative HPLC analysis showed the presence of the required sulphonamide (0.78 g, 32% yield). IR 1705 cm$^{-1}$ (C=O) (run as thin film).

EXAMPLE 3

PREPARATION OF 5-(2-CHORO-α,α,α-TRIFLUORO-4-TOLYLOXY)-N-METHANE SULPHONYL-2-NITROBENZAMIDE a. Preparation of 3-(2-chloro-α,α,α-trifluoro-4-tolyloxy) benzamide Apparatus A 500 ml doublejacketted reactor with a bottom run off fitted with a 4 blade stirrer, thermometer, a reflux condenser and a dropping funnel. A cooled mixture of ethylene glycol/water (50/50) was circulated through the reactor jacket to attain the desired temperature of the reaction mixture.

Procedure

Ammonium hydroxide (35%, 64.6 g, 1.254 mol) and DCM (200 ml) were charged to the reactor and cooled to about 2° C. with agitation. A solution of 3-(2-chloro-α,α, α-trifluoro-4-tolyloxy)benzoyl chloride (100 g, 0.243 mol) in DCM (100 ml) was added at 2°–10° C., over 35 minutes. The resulting mixture stirred for further 30 minutes at 10° C. and then allowed to warm to room temperature. Due to poor phase separation, additional DCM (250 ml) and water (300 ml) was added. The separated organic phase was washed with water until neutral to Brilliant Yellow test paper (3×135 ml), dried over anhydrous magnesium sulphate, filtered (cake washed with 2×150 ml DCM portions) and solvent evaporated from the combined filtrates in vacuo at 50° C./40 mmHg to afford an off-white powder.

The product was analysed by liquid chromatography using as eluent a mixture of water (520 ml), acetonitrile (470 ml) and glacial acetic acid (10 ml) at a flow rate of 1.5 ml/min.

Weight obtained 82.0 g

Product strength 88% by lc area.

Yield 94% based on the acid chloride.

Purification of Crude Product

A sample of the crude product (74 g) was dissolved in ethyl acetate (125 ml) at reflux (71° C). Hexane (315 ml) was added in 25 ml portions until the solution became slightly turbid. The resulting mixture was maintained at reflux for 15 minutes and then cooled slowly to 10° C. to initiate crystallisation. The white powder product was collected, washed with hexane (2×100 ml) and dried in vacuo at 50° C./15 mmHg.

Weight obtained - 36.9 g

Product strength - 96.8% by lc area.

A second crop from the mother liquors was also obtained.

Weight obtained - 13.8 g

Product strength - 95.7% by lc area.

Total recovery of Product (Crops 1 & 2) was approximately 75% on the crude product.

b. Nitration of 3-(2-chloro-α,α,α-trifluoro-4-tolyloxy) benzamide

Apparatus

A jacketed 500 ml reaction vessel equipped with a 4 blade stirrer and a thermocouple contained in a glass sheath. Cooling of the reactor was provided by circulating a chilled mixture of ethylene glycol/water, through the jacket.

Procedure

Sulphuric acid was diluted with water, at 15°–20° C., to adjust the acid strength to approximately 94% wt/wt and then cooled to −5° to −7° C. The product of step (a) (25 g, 0.079 mol) and NAPS acid (33%, 15.9 g, 0.084 mol) were divided into 5 equal portions. The first portion of step (a) product was added to the sulphuric acid, stirred for 5 minutes and then immediately followed by dropwise addition of an equivalent amount of NAPS acid at −5° to −8° C. After stirring for 2 minutes, subsequent portions of step (a) product and NAPS acid were added in a similar fashion. After the final addition of NAPS acid was made, the reaction mixture was stirred at −6° C. to −8° C. for 140 minutes.

Work-up

The reaction mixture was drowned into a stirred mixture of ice/water (400 g), below 20° C., over approximately 30 minutes. The resulting suspension was filtered, product washed acid-free with cold water and dried in vacuo at 60°–70° C./30 mmHg to afford an off-white powder.

Weight obtained - 25.5 g

Analysis of Crude Product

Isolated product was analysed by liquid chromatography eluting with a mixture of 56% 0.5 w/w phosphoric acid in water and 44% acetonitrile at a flow rate of 1.5 ml/min and indicated the following products:

| Required 2-nitro product | 66.2% wt/wt |
| 4-nitro isomer | 20.2% wt/wt |
| dinitro isomer | 5.6% wt/wt |
| Unconverted starting material | 3.6% wt/wt |

Other minor impurities were not identified.

The yield of 2-nitro product was 59% based on starting material consumed.

Purification

Purification of crude material by recrystallisation techniques did not separate the 4-nitro isomer efficiently from the main product. However a sample containing 78% 5-(2-chloro-α,α,α-trifluoro-4-tolyloxy)-2-nitrobenzamide and 12% 5-(2-chloro-α,α,α-trifluoro-4-tolyloxy)-4-nitrobenzamide was obtained.

c. Methanesulfonylation of Mixed Nitroamide Isomers from Step (b) Apparatus 100 ml RB flask fitted with a paddle stirrer, a nitrogen inlet, reflux condenser, thermometer and a dropping funnel.

Procedure

The mixture of isomers from step (b) (4 g, 10 mmol) was dissolved in THF (40 ml), under a nitrogen blanket, followed by the addition of pulverised sodium hydroxide (2 g, 50 mmol), potassium carbonate (2.35 g, 17 mmol) and tetrabutylammonium hydrogen sulphate (0.17 g, 10.5 mmol). The contents were heated to 55° C., held for 30 minutes at 55°±2° C. (a deep red coloured suspension) and followed by the addition of methanesulfonyl chloride (1.54 g) solution in THF (10 ml) over 15 minutes, at 50°–55° C. The reaction mixture was left stirring at 55° C. for 4.5 hours. Lc analysis indicated about 6% of the starting material was left, so additional methanesulfonyl chloride (0.1 g) was added, reaction left stirring for a further 2.5 hours and then cooled to the room temperature.

Work-up

Water (30 ml) was added to the stirred reaction mixture at 25°–30° C. followed by dilute hydrochloric acid until mixture was acid to Congo Red test paper. The acidic mixture was extracted with ethyl acetate (2×30 ml), combined extracts water washed, dried over anhydrous magnesium sulphate, filtered and the solvent evaporated in vacuo at 50° C./30 mmHg to afford the crude product as a tar.

Weight obtained 4.9 g

Analysis of Crude Product

Liquid chromatography analysis of the isolated product on SPHERISORB S 5ODS™ (25 cm×4.6 mm) eluting with water (626 ml), formic acid (1.4 ml), sodium hydroxide (1N, to pH 3.3) and acetonitrile (400 ml) indicated:

| | |
|---|---|
| 5-(2-choro-α,α,α-trifluoro-4-tolyloxy)-N-methane sulphonyl-2-nitrobenzamide | 15.2% wt/wt |
| 2-nitro-3-tolyloxy isomer | 6.2% wt/wt |
| 4-nitro-5-tolyloxy isomer | 1.0% wt/wt |
| Unreacted starting material | 2.3% wt/wt |

Other impurity peaks were not identified.

The yield of product was approximately 19% based on converted starting material.

d. Methanesulfonylation of Mixed Nitroamide Isomers From Step (b) in a Catalytic Two Phase System Apparatus A 250 ml flask fitted with a paddle stirrer, reflux condensor, a thermometer and a dropping funnel.

Procedure

A mixture of 2-nitro (69%) and 4-nitro (14%) isomers from Step (b) (3 g, 6.9 mmol) was dissolved in toluene (30 ml) followed by the addition of 50% aqueous sodium hydroxide solution (50% w/w, 20 ml) and benzyltriethyl ammonium chloride (0.3 g, 1.32 mmol). The heterogeneous mixture heated to 55° C. and held for 30 minutes to afford a deep red top phase. A solution of methanesulfonyl chloride in toluene (5 ml) was added at 50°–55° C., over 20 minutes (exothermic), and the reaction mixture left stirring at 55°±2° C. for 8 hours and then cooled to the room temperature.

Work-up

Water (25 ml) was added to the stirred reaction mixture. After cooling to 0° C., the mixture was acidified (Congo Red test paper) with concentrated hydrochloric acid at 0°–15° C., over 30 minutes. The organic layer was separated, aqueous phase "re" extracted with portions of fresh toluene (2×15 ml), combined organic phase was washed with water (2×20 ml) and finally the toluene was evaporated in vacuo at 50° C./15 mmHg to give an off-white powder.

Weight obtained 3.2 g

Analysis of Isolated Product

The product was analysed by liquid chromatography on SPHERISORB S 5ODS™ (25 cm×4.6 mm) eluting with water (626 ml), formic acid (1.4 ml), sodium hydroxide (1N, to pH 3.3) and acetonitrile (400 ml) at a flow reate of 2 ml/min and at 40° C. The analysis indicated:

| | |
|---|---|
| 5-(2-choro-α,α,α-trifluoro-4-tolyloxy)-N-methane sulphonyl-2-nitrobenzamide | 29.9% wt/wt |
| 2-nitro-3-tolyloxy isomer | 9.2% wt/wt |
| Unconverted starting material | 11.9% wt/wt |

Yield of product was 48% on starting material consumed.

EXAMPLE 4

METHANESULFONYLATION OF 3-(2-CHLORO-α,α,α-TRIFLUORO-4-TOLYLOXY)BENZAMIDE IN THF

Apparatus

A 250 ml round bottomed flask fitted with a nitrogen inlet, condenser, thermometer and a dropping funnel.

Procedure 3-(2-chloro-α,α,α-trifluoro-4-tolyloxy)benzamide from Example 3(a) (4 g, 12.6 mmol) was dissolved in THF (40 ml) at room temperature under a nitrogen blanket. Sodium hydroxide (2.6 g, 65 mmol), potassium carbonate (3.1 g, 22 mmol) and tetrabutylammonium hydrogen sulphate (0.224 g, 0.7 mmol) were charged and then heated to 55° C.±2° C. for 45 minutes to give an orange/red coloured suspension. Methanesulfonyl chloride (1.98 g) in THF (10 ml) was added over 25 minutes (cooling applied to control the exotherm), and the reaction temperature was maintained at 55°–57° C. for 18 hours. After analysis, additional methanesulfonyl chloride (0.67 g) was added and reaction mixture was stirred for a further 2 hours at 55° C. and then cooled to room temperature.

Work-up

Water (25 ml) was added and the mixture acidified with dilute hydrochloric acid until acid to Congo Red test paper. The resulting mixture was extracted with ethyl acetate (2×20 ml). After washing with water (2×8 ml), drying over anhydrous magnesium sulphate and filtering, the solvent was evaporated in vacuo at 50° C./20 mmHg to give an off-white powder.

Weight obtained 4.60 g

Analysis of Isolated Product

The product was analysed by liquid chromatography on SPHERISORB S 5ODS™ (25 cm×4.6 mm) eluting with water (520 ml) acetonitrile (470 ml) and glacial acetic acid (10 ml) with a flow rate of 1.5 ml/min. The analysis indicated:

| | |
|---|---|
| 3-(2-chloro-α,α,α-trifluoro-4-tolyloxy) methane sulphonylbenzamide | 53.8% wt/wt |
| 3-(2-chloro-α,α,α-trifluoro-4-tolyloxy)benzoic acid | 5.0% wt/wt |
| Unconverted starting material | 15.2% wt/wt |

Yield of product was 71% based on starting material consumed.

EXAMPLE 5

METHANESULFONYLATION OF 3-(2-CHLORO-α,α,α-TRIFLUORO-4-TOLYLOXY)BENZAMIDE-USING A CATALYTIC TWO PHASE SYSTEM

Apparatus 250 ml RB flask fitted with a paddle stirrer, thermometer, condenser and a dropping funnel.

Procedure 3-(2-Chloro-α,α,α-trifluoro-4-tolyloxy)benzamide from Example 3(a) (2 g, 6.4 mmol) was dissolved in toluene (25 ml) at room temperature followed by the addition of benzyltriethylammonium chloride (0.2 g, 0.9 mmol) and aqueous sodium hydroxide solution (50%, 10 ml). The reaction mixture was heated to 55° C., held for 45 minutes at 55° C. to afford a deep orange top layer. Methanesulfonyl chloride (1.0 g) in toluene (5 ml) was added over 20 minutes (slight exotherm) and reaction was stirred at 55°±2° C. for 20 hours. After analysis, additional methanesulfonyl chloride (0.35 g) was added, and the reaction mixture was stirred for further 3 hours at 55°+2° C. before being cooled to 0° C.

Work-up

Water (25 ml) was added followed by concentrated hydrochloric acid at 0°–20° C., over 30 minutes, until acid to Congo Red test paper. The organic phase was separated and the aqueous phase was extracted with fresh toluene (2×10 ml). The combined organic phase was water washed (2×25 ml) and the toluene was removed in vacuo at 50° C./15 mmHg to afford a tacky solid.

Weight obtained - 2.2 g

Analysis of Isolated Product

The product was analysed by liquid chromatography on SPHERISORB S 5ODS™ (25 cm×4.6 mm) eluting with water (520 ml) acetonitrile (470 ml) and glacial acetic acid (10 ml) with a flow rate of 1.5 ml/min. The analysis indicated:

| | |
|---|---|
| 3-(2-chloro-α,α,α-trifluoro-4-tolyloxy) methane sulphonyl benzamide | 26.4% wt/wt |
| Unreacted starting material | 52.0% wt/wt |

Yield of product was 48% on starting material consumed.

SCHEME I

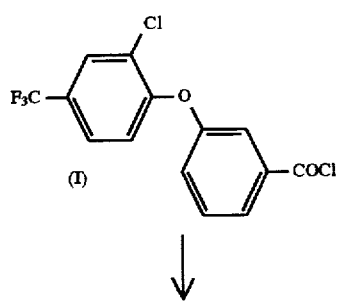

-continued
SCHEME I

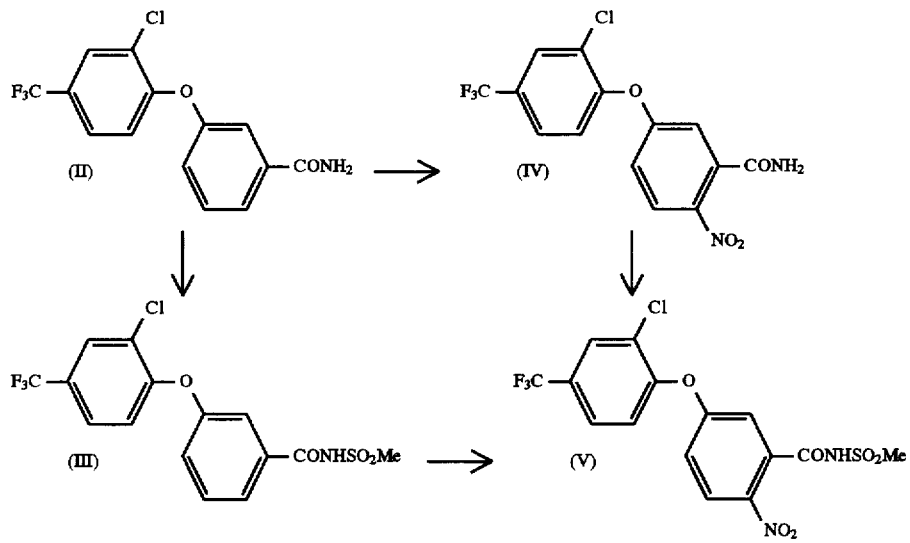

We claim:

1. A process for the production of an N-(alkylsulfonyl) amide, the process comprising reacting a primary amide with a sulfonylhalide in the presence of a base which is sufficiently strong to cause at least partial deprotonation of the amide, the base comprising an alkali or alkaline earth metal, ammonium or quaternary ammonium hydroxide, sodium amide, potassium bistrimethylsilylamide, a reducing metal or an alkali metal carbonate.

2. A process as claimed in claim 1 wherein the solvent is a co-ordinating solvent such as a cyclic ether, a ketone, a nitrile or a dialkylamide or a two phase system comprising an aqueous phase and an organic phase.

3. A process as claimed in claim 2, wherein the solvent is tetrahydrofuran or a two phase system comprising an aqueous phase and toluene.

4. A process as claimed in claim 1, wherein the reaction mixture further comprises an entity having an organic cation.

5. A process as claimed in claim 1, comprising the initial step of converting an acyl halide to an amide by reaction with ammonia.

6. A process for the synthesis of 5-(2-chloro-α,α,α-trifluoro-4-tolyloxy)-N-methanesulphonyl-2-nitrobenzamide (fomesafen) from 3-(2-chloro-α,α,α-trifluoro-4-tolyloxy) benzamide, the process comprising, in any order, the steps of nitration and sulphonylation by a process as claimed in claim 1.

7. A process as claimed in claim 6, the process comprising reacting 3-(2-chloro-α,α,α-trifluoro-4-tolyloxy) benzamide with methane sulphonyl chloride in the presence of a base which is sufficiently strong to be capable of at least partially deprotonating the amide, and nitrating the product.

8. A process as claimed in claim 6, the process comprising reacting 5-(2-chloro-α,α,α-trifluoro-4-tolyloxy)-2-nitrobenzamide with methane sulphonyl chloride in the presence of a base which is sufficiently strong to be capable of at least partially deprotonating the amide.

9. A process according to claim 4 wherein the entity having an organic cation comprises tetrabutylammonium hydrogen sulfate.

* * * * *